United States Patent [19]

Horváth et al.

[11] Patent Number: 5,171,910
[45] Date of Patent: Dec. 15, 1992

[54] STATIONARY AQUEOUS ACID PHASE TRANSITION METAL CATALYSTS FOR REDUCTION OF AROMATICS (C-2503)

[75] Inventors: István T. Horváth, Yardley, Pa.; Raymond A. Cook, Bethlehem Township, Hunterdon County, N.J.

[73] Assignee: Exxon Research and Engineering Company, Florham Park, N.J.

[21] Appl. No.: 774,936

[22] Filed: Oct. 11, 1991

Related U.S. Application Data

[62] Division of Ser. No. 576,754, Sep. 4, 1990, Pat. No. 5,100,851.

[51] Int. Cl.$^5$ .................................................. C07C 5/10
[52] U.S. Cl. ..................................... 585/266; 585/269
[58] Field of Search ................................. 585/266, 269

[56] References Cited

U.S. PATENT DOCUMENTS

| | | | |
|---|---|---|---|
| 4,212,990 | 7/1980 | Yasuhara et al. | 585/269 |
| 4,284,835 | 8/1981 | Kim et al. | 585/277 |
| 4,506,030 | 3/1985 | Jones | 585/269 |

Primary Examiner—Anthony McFarlane
Assistant Examiner—C. Everhart
Attorney, Agent, or Firm—Linda M. Scuorzo

[57] ABSTRACT

The present invention provides a catalyst for hydrogenation of aromatic compounds, which comprises a hydrophilic support material; and a stationary aqueous acid phase supported by the hydrophilic support material, the aqueous acid having a transition metal catalyst dissolved therein, Preferably, the solid hydrophilic support material is an acidic material, such as an acid-treated clay.

The foregoing catalyst is particularly useful in hydrogenating aromatic hydrocarbons.

6 Claims, 2 Drawing Sheets

STATIONARY AQUEOUS ACID PHASE TRANSITION METAL CATALYSTS FOR REDUCTION OF AROMATICS (C-2503)

This is a division of application Ser. No. 576,754, filed Sep. 4, 1990, now U.S. Pat. No. 5,100,851.

FIELD OF THE INVENTION

This invention relates to catalysts and the catalytic hydrogenation of aromatics compounds. More particularly, the invention relates to stationary aqueous acid phase homogeneous transition metal catalysts and their use in hydrogenation of aromatic compounds.

BACKGROUND OF THE INVENTION

There is a wide variety of catalysts used in the hydrogenation of organic compounds, including aromatic compounds. Most typically, the catalysts used are solids, such as transition metals, which are dispersed on a solid catalyst support. The advantages and disadvantages of such catalysts are, of course, well known. Among their advantages are their physical strength, typically large surface area, ease of manufacture and often commercial availability. Among the disadvantages of these typical catalysts are their varying activity and selectivity. For example, it is generally necessary to use relatively severe hydrogenation conditions when these typical catalysts are used in hydrogenating organic compounds and these conditions typically lead to cracking and other undesirable side reactions. Therefore, it is an object of the present invention to provide new and improved catalysts and methods for hydrogenating organic compounds, such as aromatic compounds.

SUMMARY OF THE INVENTION

Accordingly, the present invention provides a catalyst for hydrogenation of aromatic compounds, which comprises a hydrophilic support material; and a stationary aqueous acid phase supported by the hydrophilic support material, the aqueous acid having a transition metal catalyst dissolved therein. Preferably, the solid hydrophilic support material is an acidic material, such as an acid-treated clay.

The foregoing catalyst is particularly useful in hydrogenating aromatic hydrocarbons.

These and other features of the present invention will become more readily understood upon a reading of the "Detailed Description" which follows in conjunction with the accompanying drawings.

THE DRAWINGS

FIG. 1 graphically illustrates the hydrogenation of benzene to cyclohexane in accordance with the present invention.

FIG. 2 pictorially demonstrates the hydrogenation, according to the present invention, of a hydrocarbon feed containing a mixture of aromatic hydrocarbons.

DETAILED DESCRIPTION OF THE INVENTION

Figure 1:
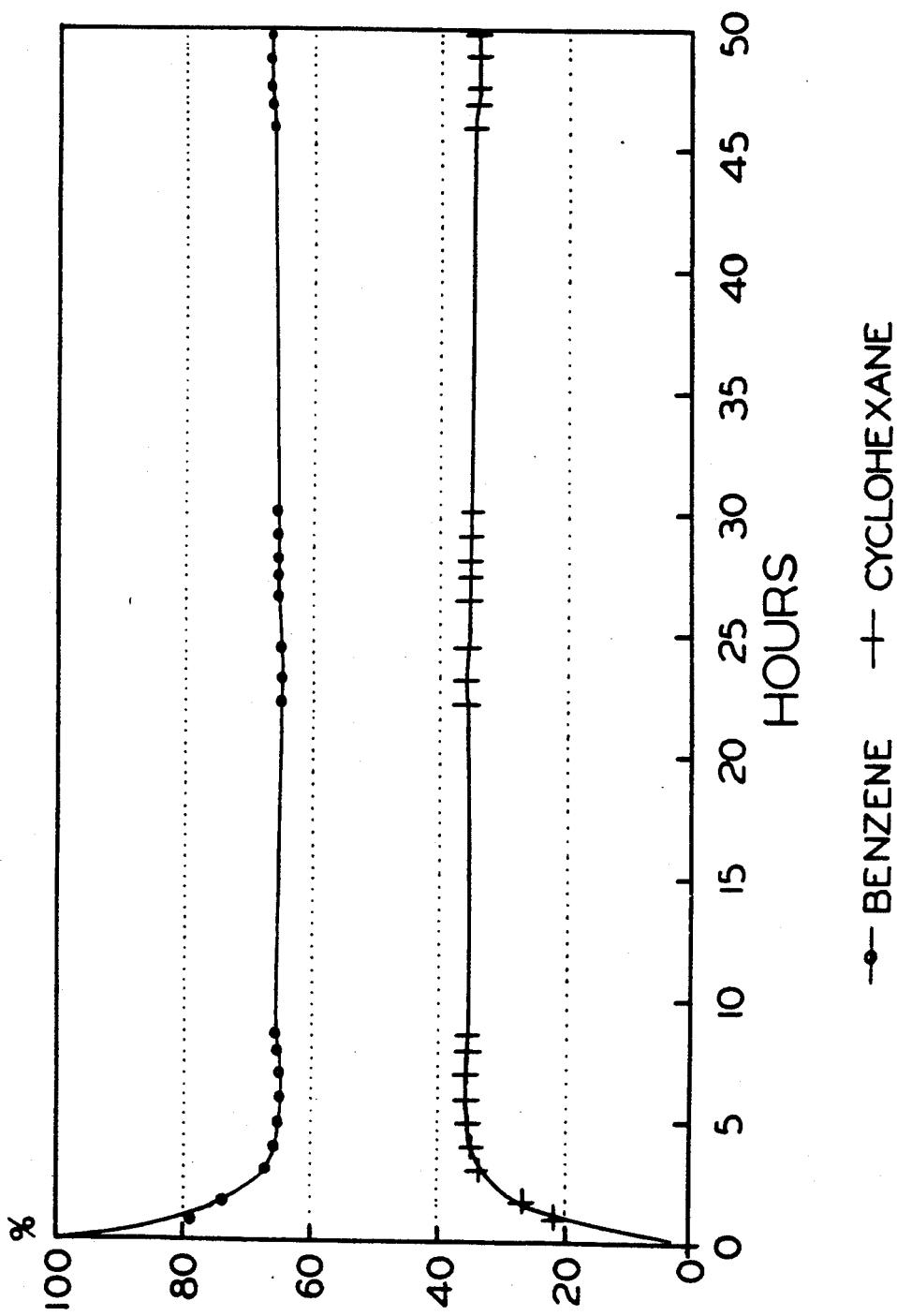

The catalyst useful in hydrogenating aromatic compounds according to the present invention includes a solid hydrophilic carrier or support. In general, the support will be a porous solid material. For example, materials having a pore volume relative to solid weight of from about 0.1 to 1.5 cubic centimeters per gram, with a preferred range of from about 0.4 to 1.0 are especially useful supports. The macropore volume of the support material should be at least 10% of the total pore volume. By macropore volume is meant pores having diameters greater than 100 Angstroms.

Specific examples of such solid materials useful in the practice of the present invention are silica, clay, alumina, silica/alumina, acid treated clay and titania. Indeed, it is particularly preferred in the practice of the present invention to use acidic support materials such as silica/alumina, clay and, even more particularly, acid treated clay.

The catalyst of the present invention also includes a stationary aqueous acid phase; i.e., the aqueous acid phase does not circulate or flow as a liquid, but is immobile and supported on the solid phase. Typical stationary aqueous acid liquid phase materials that can be used in the practice of the present invention include aqueous solutions of $CH_3COOH$, $CF_3COOH$, $H_3PO_4$, HF, HCl, $H_2SO_4$, $CH_3SO_3H$, $CF_3SO_3H$, $BF_3$ and mixtures thereof. Indeed, it is particularly preferred in the practice of the present invention to use an an equimolar amount of $BF_3$ and water, $BF_3 \cdot H_2O$ as the aqueous acid phase.

The volume of stationary aqueous acid phase supported by the solid in the catalyst of the present invention will generally be a predetermined maximum amount that can be supported without causing the particulate of the solid support to stick together. Typically, the amount of aqueous acid phase will be less than that of the pore volume of the specific support employed. Indeed, it is preferred that the amount of acid phase will be about 10% less than the pore volume of the support. Thus, for example, about 1.3 cc of aqueous acid will be used with a solid support having a pore volume of 1.5 cc/gm.

Finally, the catalyst of the present invention includes a transition metal compound which is soluble in the aqueous acid phase. The transition metals employed herein include cobalt, rhodium, iridium, palladium, platinum, ruthenium, rhenium and mixtures thereof.

Examples of acid soluble transition metal compounds include $PtCl_2(PR_3)_2$ (R=alkyl, aryl, aralkyl), $PtCl_2(MeCN)_2$, $PdCl_2(MeCN)_2$ (Me=methyl) and the like. When R is selected from alkyl groups it generally will have from 1 to 10 carbon atoms. Where R is an aryl group it generally will have 6 carbon atoms. When R is an aralkyl it will have about 7 to 10 carbon atoms. In the practice of the present invention, $PtCl_2(MeCN)_2$ is particularly preferred.

The amount of transition metal compound to be dissolved in the aqueous phase will range generally in the range of about 0.1 wt % to 10 wt % of the transition metal compound and preferably from about 0.5 wt % to 3 wt %.

The transition metal compound chosen preferably will be one which is relatively insoluble in the organic material to be hydrogenated with the composite catalyst and also relatively insoluble in the hydrogenation products.

In preparing the catalyst for use in hydrogenation of aromatic compounds, the transition metal complex is first dissolved in the aqueous acid phase, then the solution is impregnated onto the support material by the incipient wetness technique. The catalyst is used without further treatment.

Aromatic organic compounds may be hydrogenated in the presence of the above described catalyst at temperatures as low as 0° C. and under hydrogen pressures of about 15 psig; however, it is preferred that the temperature be at least 25°0 C. and the hydrogen pressure at least 200 psig. Temperatures may be as high as 150° C., but it is preferred that no higher than about 75° C. be employed. Hydrogen pressures not exceeding 1000 psig are also preferred. Space velocity defined as gram of feed per gram of catalyst per hour (WHSV) should be at least 0.1 and not over 20. However, it is preferable that WHSV be at least 0.5 and not above 10.

The hydrogenation processes according to the present invention may be conducted in batch, semicontinuous or continuous operations for times sufficient to at least partially hydrogenate the aromatic compounds. Obviously, continuous operation is more suitable for commercial processes.

The following examples are included to further illustrate the invention and not to imply a limitation thereon.

EXAMPLE 1

Preparation of Stationary $BF_3.H_2O$ Phase Platinum Catalysts on Acidic Clay

A sample of 0.1 grams of $PtCl_2(CH_3CN)_2$ is dissolved in 1.4 grams of $BF_3.H_2O$ under $N_2$ atmosphere. The light yellow solution is impregnated onto 3 grams of acidic clay by the incipient wetness technique. The catalyst is used without further treatment.

EXAMPLE 2

Hydrogenation of Benzene with Stationary $BF_3.H_2O$ Phase Platinum Catalysts on Acidic Clay in Batch Reactor The experiments were carried out in a 300 ml Hastelloy (H) autoclave equipped with an impeller type stirrer operating at 1000 rpm, a temperature measuring means, a gas feed piping, and a dip-leg with a 7 micron filter for sample withdrawing. The autoclave was charged with 8.75 grams of stationary $BF_3.H_2O$ phase platinum catalyst on acidic clay [5 grams acidic clay (100–200 mesh), 3.5 grams $BF_3.H_2O$ and 0.25 grams $PtCl_2(CH_3CN)_2$], 48 grams of heptane and 1 gram of decane under $N_2$. The autoclave was sealed and heated to 40° C. When the solution has reached the reaction temperature, 20 grams of heptane and 32 grams of benzene was pressured into the autoclave with 800 psig $H_2$ gas pressure.

The progress of the hydrogenation was followed by GC analysis of samples taken periodically and the results are summarized in Table 1. $^1H$ NMR spectra of the samples show no formation of any partially reduced products.

TABLE 1

| Time (min) | 10 | 20 | 30 | 60 | 120 |
|---|---|---|---|---|---|
| Benzene (%) | 81.6 | 61.5 | 46.8 | 16.8 | 0.1 |
| c-Cyclohexane (%) | 18.3 | 38.6 | 53.2 | 83.2 | 99.8 |

EXAMPLE 3

Hydrogenation of Benzene with Stationary $BF_3.H_2O$ Phase Platinum Catalysts on Acidic Clay in Continuous Reactor The experiments were carried out in a tubular trickle-bed reactor (i.d. ½″) at 20° C. and 400 psig $H_2$ pressure using 4.5 grams of stationary $BF_3.H_2O$ phase platinum catalyst on acidic clay [3 grams acidic clay (16–20 mesh), 1.4 grams $BF_3.H_2O$ and 0.1 grams $PtCl2(CH3CN)2$]. The reaction feed contained 30% benzene, 10% decane and 60% heptane and was introduced with 0.25 ml/min feed rate. The $H_2$ feed rate was 80 scc/min. Under these conditions 38% of the benzene is hydrogenated to cyclo-hexane as shown on FIG. 1.

EXAMPLE 4

Hydrogenation of the Mixture of Benzene, Toluene, o-Xylene, and 1,2,4 Trimethyl-Benzene with Stationary $BF_3.H_2O$ Phase Platinum Catalysts on Acidic Clay in Batch Reactor The experiments were carried out in a 300 ml Hastelloy (H) autoclave equipped with an impeller type stirrer operating at 1000 rpm, a temperature measuring means and gas feed piping. The autoclave was charged with 3.5 grams of stationary $BF_3.H_2O$ phase platinum catalyst on acidic clay [2 grams acidic clay, 1.4 grams $BF_3 H_2O$ and 0.1 grams $PtCl_2(CH_3CN)_2$], 7.5 grams of benzene, 8.85 grams of toluene, 10.19 grams of o-xylene, 11.54 grams of 1,2,4-trimethyl-benzene and 61.92 grams of decane under $N_2$. The autoclave was sealed, thermostated at 22° C. and charged with 400 psig $H_2$ gas pressure.

The progress of the hydrogenation was followed by GC analysis of samples taken periodically and the results are summarized in Table 2.

TABLE 2

| Time (hr.) | 2 | 4 | 8 | 26 |
|---|---|---|---|---|
| Benzene (%) | 90.1 | 77.8 | 53.5 | 7.6 |
| c-Hexane (%) | 9.9 | 22.1 | 46.5 | 92.4 |
| Toluene (%) | 93.3 | 84.6 | 65.7 | 17.2 |
| Me-c-hexane (%) | 6.6 | 15.5 | 34.4 | 82.8 |
| o-Xylene (%) | 97.2 | 93.6 | 85.0 | 55.2 |
| 1,2-Me$_2$-c-hexane (%) | 2.8 | 6.5 | 15.0 | 44.8 |
| 1,2,4-Me$_3$-benzene (%) | 99.1 | 98.7 | 96.3 | 85.7 |
| 1,2,4-Me$_3$-c-hexane (%) | 1.0 | 1.3 | 3.7 | 14.3 | c = cyclo
Me = methyl

EXAMPLE 5

Hydrogenation of the Mixture of Benzene, Toluene, o-Xylene, and 1,2,4 Trimethyl-Benzene with Stationary $BF_3.H_2O$ Phase Platinum Catalysts on CPG-240 Silica in Batch Reactor The experimetns were carried out in a 300 ml Hastelloy (H) autoclave equipped with an impeller type stirrer operating at 1000 rpm, a temperature measuring means and gas feed piping. The autoclave was charged with 3.5 grams of stationary $BF_3.H_2O$ phase platinum catalyst on silica [2 grams CPG 240, 1.4 grams $BF_3.H_2O$ and 0.1 grams $PtCl_2(CH_3CN)_2$], 7.5 grams of benzene, 8.85 grams of toluene, 10.19 grams of o-xylene, 11.54 grams of 1,24-trimethyl-benzene and 61.92 grams of decane under $N_2$. The autoclave was sealed, thermostated at 22° C. and charged with 400 psig $H_2$ gas pressure.

The progress of the hydrogenation was followed by GC analysis of samples taken periodically and the results are summarized in Table 3.

TABLE 3

| Time (hr.) | 2 | 4 | 8 | 24 |
|---|---|---|---|---|
| Benzene (%) | 89.8 | 78.1 | 54.3 | 13.0 |
| c-Hexane (%) | 10.2 | 22.0 | 45.7 | 87.0 |
| Toluene (%) | 93.5 | 85.2 | 66.2 | 22.2 |
| Me-c-hexane (%) | 6.5 | 14.8 | 33.7 | 77.8 |
| o-Xylene (%) | 97.4 | 93.8 | 84.6 | 57.4 |
| 1,2-Me$_2$-c-hexane (%) | 2.6 | 6.2 | 15.4 | 42.5 |
| 1,2,4-Me$_3$-benzene (%) | 99.3 | 97.9 | 95.1 | 81.4 |

TABLE 3-continued

| Time (hr.) | 2 | 4 | 8 | 24 |
|---|---|---|---|---|
| 1,2,4-Me$_3$-c-hexane (%) | 0.7 | 2.0 | 4.9 | 18.6 | c = cyclo
Me = methyl

EXAMPLE 6

Hydrogenation of the Mixture of o-Xylene, Naphthalene and Anthracene with Stationary BF$_3$.H$_2$O Phase Platinum Catalysts on Acidic Clay in Batch Reactor The experiments were carried out in a 300 ml Hastelloy (H) autoclave equipped with an impeller type stirrer operating at 1000 rpm, a temperature measuring means and gas feed piping. The autoclave was charged with 8.75 grams of stationary BF$_3$.H$_2$O phase platinum catalyst on acidic clay [5 grams acidic clay, 3.5 grams BF$_3$.H$_2$O and 0.25 grams PtCl$_2$(CH$_3$CN)$_2$], and 40 grams of heptane and N$_2$. The autoclave was sealed and heated to 75° C. When the solution has reached the reaction temperature, 42 grams of o-xylene, 21 grams of naphthalene and 0.7 grams of anthracene was pressured into the autoclave with 800 psig H$_2$ gas pressure.

Figure 2:
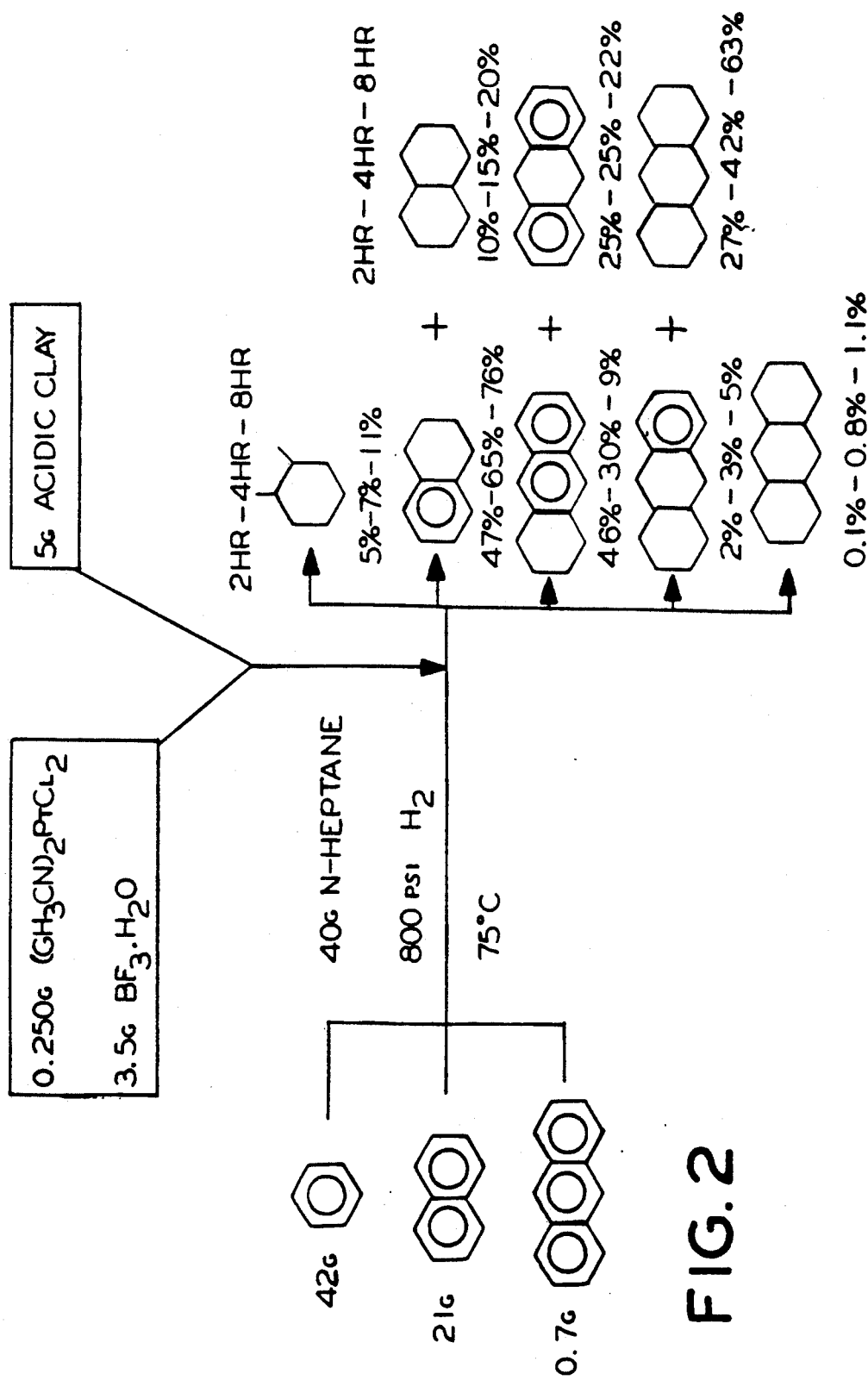

The progress of the hydrogenation was followed by GC analysis of samples taken periodically and the results are summarized in FIG. 2.

What is claimed is:

1. A process for hydrogenating aromatic compounds and mixtures thereof comprising:
   contacting an aromatic compound or mixture thereof with hydrogen in the presence of a catalyst containing a stationary aqueous acid phase containing an acid soluble transition metal compound wherein the stationary aqueous acid phase and acid soluble transition metal compound are impregnated onto a hydrophilic, porous, solid support at temperatures in the range of from about 0° C. to about 150° C. for a time sufficient to at least partially hydrogenate said aromatic compound.

2. The process of claim 1 wherein the hydrogen pressure is in the range of from about 15 psig to about 1000 psig.

3. The process of claim 2 wherein the support material is selected from the group consisting of silica, clay, alumina, silica/alumina and titania.

4. The process of claim 2 wherein the aqueous acid is selected from the group consisting of CH$_3$COOH, CF$_3$COOH, H$_3$PO$_4$, HF, HCl, H$_2$SO$_4$, CH$_3$SO$_3$H, CF$_3$SO$_3$H, BF$_3$ and mixtures thereof.

5. The process of claim 4 wherein the temperature is in the range of from about 25° C. to about 75° C.

6. The process of claim 5 wherein the aqueous acid is BF$_3$.H$_2$O and the transition metal compound is PtCl$_2$(CH$_3$CN)$_2$.

* * * * *